United States Patent [19]

Chandraratna

[11] Patent Number: 5,599,819
[45] Date of Patent: Feb. 4, 1997

[54] ACETYLENES DISUBSTITUTED WITH A THIENYL OR FURYL GROUP AND A 2-SUBSTITUTED CHROMANYL, THIOCHROMANYL OR 1,2,3,4 - TETRAHYDROQUINOLINYL GROUP HAVING RETINOID-LIKE ACTIVITY

[75] Inventor: Roshantha A. S. Chandraratna, El Toro, Calif.

[73] Assignee: Allergan

[21] Appl. No.: 458,389

[22] Filed: Jun. 2, 1995

Related U.S. Application Data

[62] Division of Ser. No. 385,000, Feb. 7, 1995, which is a division of Ser. No. 144,178, Oct. 27, 1993, Pat. No. 5,407,937, which is a division of Ser. No. 967,630, Oct. 28, 1992, Pat. No. 5,272,156, which is a division of Ser. No. 732,270, Jul. 18, 1991, Pat. No. 5,183,827, which is a division of Ser. No. 409,476, Sep. 19, 1989, Pat. No. 5,045,551.

[51] Int. Cl.$^6$ .................................................. A61K 31/50
[52] U.S. Cl. .................................................. 514/314; 546/166
[58] Field of Search .............................. 514/314; 546/166

[56] References Cited

U.S. PATENT DOCUMENTS

| | | |
|---|---|---|
| 4,096,341 | 6/1978 | Frazer . |
| 4,326,055 | 4/1982 | Loeliger . |
| 4,391,731 | 7/1983 | Boller et al. ............... 252/299.62 |
| 4,537,903 | 8/1985 | Chang et al. ............... 514/456 |
| 4,695,649 | 9/1987 | Magami et al. . |
| 4,723,028 | 2/1988 | Shudo . |
| 4,739,098 | 4/1988 | Chandraratna . |
| 4,740,519 | 4/1988 | Shroot et al. . |
| 4,810,804 | 3/1989 | Chandraratna . |
| 4,826,969 | 5/1989 | Maignan et al. . |
| 4,826,984 | 5/1989 | Berlin et al. ............... 546/134 |
| 4,855,320 | 8/1989 | Chatterjee et al. . |
| 4,895,868 | 1/1990 | Chandraratna . |
| 4,927,947 | 5/1990 | Chandraratna ............... 549/484 |
| 4,980,369 | 12/1990 | Chandraratna . |
| 4,992,468 | 2/1991 | Chandraratna . |
| 5,006,550 | 4/1991 | Chandraratna . |
| 5,013,744 | 5/1991 | Chandraratna . |
| 5,015,658 | 5/1991 | Chandraratna . |
| 5,023,341 | 6/1991 | Chandraratna . |
| 5,037,825 | 8/1991 | Klaus et al. ............... 514/233.8 |
| 5,045,551 | 9/1991 | Chandraratna . |

(List continued on next page.)

FOREIGN PATENT DOCUMENTS

| | | |
|---|---|---|
| 0098591 | 1/1984 | European Pat. Off. . |
| 0130795 | 1/1985 | European Pat. Off. . |
| 176034A | 4/1986 | European Pat. Off. . |
| 0176032 | 4/1986 | European Pat. Off. ......... C07C 65/38 |
| 0176033 | 4/1986 | European Pat. Off. ......... C07D 261/18 |
| 170105A | 7/1987 | European Pat. Off. . |
| 0253302 | 1/1988 | European Pat. Off. ......... C07D 213/16 |
| 0272921 | 6/1988 | European Pat. Off. . |
| 0284288 | 9/1988 | European Pat. Off. . |
| 0303915 | 2/1989 | European Pat. Off. ......... A61K 31/255 |
| 0315071 | 5/1989 | European Pat. Off. ......... C07C 63/66 |
| 0350846 | 7/1989 | European Pat. Off. . |
| 3316932 | 11/1983 | Germany . |
| 3524199 | 1/1986 | Germany . |
| 3602473 | 7/1987 | Germany ................ C07C 43/215 |
| 3708060 | 9/1987 | Germany . |
| 3715955 | 11/1987 | Germany . |
| 2190378 | 11/1987 | United Kingdom . |
| 8500806 | 2/1985 | WIPO . |
| 8504652 | 10/1985 | WIPO . |
| WO9116051 | 10/1991 | WIPO . |
| WO9206948 | 4/1992 | WIPO . |

OTHER PUBLICATIONS

A General Synthesis of Terminal and Internal Arylalkynes by the Palladium–Catalyzed Reaction of Alkynylzinc Reagents with Aryl Halides by Anthony O. King and Ei-ichi Negishi, *J. Org. Chem.* 43 No. 2, 1978 p. 358.

Conversion of Methyl Ketones into Terminal Acetylenes and (E)-Tri-substituted Olefins of Terpenoid Origin by Ei-ichi, Anthony O. King, and William L. Klima, *J. Org. Chem.* 45 No. 12, 1980 p. 2526.

Sporn et. al. in *J. Amer. Acad. Derm.* 15:756–764 (1986).

A Convenient Synthesis of Ethynylarenes and Diethynylarenes by S. Takahashi, Y. Kuroyama, K. Sonogashira, N. Hagihara, Synthesis 1980 pp. 627–630.

Shudo et al. in *Chem. Phar. Bull.* 33:404–407 (1985).

Kagechika et. al. in *J. Med. Chem.* 31:2182–2192 (1988).

Chemistry and Biology of Synthetic Retinoids by Marcia I. Dawson and William H. Okamura, published by CRC Press Inc., 1990, pp. 334–335, 354.

Synthesis of 2,2'–Diacycl–1,1'–biaryls. Regiocontrolled Protection of . . . by Mervic, et al, *J. Org. Chem.*, No. 45, pp. 4720–4725, 1980.

A Dopamine Receptor Model and Its Application in the Design of a New Class of Rigid Pyrrolo[2,3–g]isoquinoline Antipsychotics, Gary L. Olson, et al. *American chemical Society*, 1981, Vo. 24, No. 9, pp. 1026–1031.

(List continued on next page.)

Primary Examiner—Donald G. Daus
Attorney, Agent, or Firm—Gabor L. Szekeres; Robert J. Baran; Martin A. Voet

[57] ABSTRACT

Retinoid-like activity is exhibited by compounds of the formula

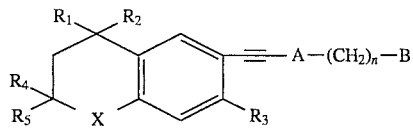

where X is NR'; where R' is hydrogen or lower alkyl; $R_1$, $R_2$ and $R_3$ are hydrogen or lower alkyl; $R_4$ and $R_5$ are hydrogen or lower alkyl with the proviso that $R_4$ and $R_5$ cannot both be hydrogen, A is thienyl, furyl; n is 0-5, and B is H, —COOH or a pharmaceutically acceptable salt, ester or amide thereof, —$CH_2OH$ or an ether or ester derivative, or —CHO or an acetal derivative, or —$COR_1$ or a ketal derivative where $R_1$ is —$(CH_2)_mCH_3$ where m is 0-4, or a pharmaceutically acceptable salt thereof.

17 Claims, No Drawings

U.S. PATENT DOCUMENTS

| | | | |
|---|---|---|---|
| 5,053,523 | 10/1991 | Chandraratna . | |
| 5,068,252 | 11/1991 | Chandraratna . | |
| 5,089,509 | 2/1992 | Chandraratna . | |
| 5,130,335 | 7/1992 | Chandraratna . | |
| 5,134,159 | 7/1992 | Chandraratna . | |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraratna | 514/365 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1993 | Chandraratna | 564/163 |
| 5,354,752 | 10/1994 | Chandraratna | 514/252 |
| 5,380,877 | 1/1995 | Chandraratna | 549/60 |
| 5,391,753 | 2/1995 | Chandraratna | 546/63 |
| 5,399,561 | 3/1995 | Chandraratna | 514/252 |
| 5,399,586 | 3/1995 | Davies etal. | 514/448 |
| 5,407,937 | 4/1995 | Chandraratna | 514/256 |
| 5,414,007 | 5/1995 | Chandraratna | 514/365 |
| 5,426,118 | 6/1995 | Chandraratna et al. | 514/337 |
| 5,434,173 | 7/1995 | Chandraratna | 514/354 |

OTHER PUBLICATIONS 6.2.3 Conformational Restriction, Williams, et al., *Drug Discovery and Development*, 1987 The Humana Press, pp. 45–55.

V. Retinoid Structure–Biological Activity Relationships, Chemistry and Biology of Synthetic Retinoids, pp. 324–356, 1990.

Davis et al. *J. Organomettalic Chem* 387 (1990) 381–390.

Effects of 13–Cis–Retinotic Acid, All–Trans–retinoic Acid, and Acitretin on the Proliferation, Lipid Synthesis and Keratin Expression of Cultured Human Sebocytes In Vitro, C. C. Zouboulis, *The Journal of Investigative Dermatology*, vol. 96, No. 5, May 1991, pp. 792–797.

Organ maintenance of human sebaceous glands: in vitro effects of 13–cis retinoic acid and testosterone, John Ridden, et al., Journal of Cell *Science*, vo. 95, 1990, pp. 125–136.

Characterization of Human Sebaceous Cells In Vitro, Thomas I. Doran, et al., *The Journal of Investigative Dermatology*, vol. 96, No. 3, Mar. 1991.

Synthesis and Evaluation of Stilbene and Dihydrostilbene Derivatives as Potential Anticancer Agents That Inhibit Tubulin Polymerization by Cushman, Mark et. al. *J. Med. Chem* 1991, 34, 2579–2588.

Synthesis and Evaluation of New Protein–Tyrosine Kinase Inhibitors. Part 1. Pyridine–Containing Stilbenes and Amides by Cushman, Mark et al. *Bioorganic & Medicinal Chemistry Letters*, vol. 1, No. 4, pp. 211–214, 1991.

Di–and Tri–methoxystyryl Derivatives of Heterocyclic Nitrogen Compounds by Bahner, C. T. et al. Arzneim–Forsch./Drug Res, 31 (I), Nr. 3 (1981).

Retinobenzoic acids. 3. Structure–Activity Relationships of retinoidal Azobenzene–4–carboxylic acids and Stilbene–4–carboxylic acids by H. Kagechika et al., *Journal of Medicinal Chemistry*, 1989, 32, pp. 1098–1108.

ACETYLENES DISUBSTITUTED WITH A THIENYL OR FURYL GROUP AND A 2-SUBSTITUTED CHROMANYL, THIOCHROMANYL OR 1,2,3,4-TETRAHYDROQUINOLINYL GROUP HAVING RETINOID-LIKE ACTIVITY

CROSS-REFERENCE TO RELATED APPLICATION

The present application is a divisional of application Ser. No. 08/385,000 filed on Feb. 7, 1995, which is a divisional of application Ser. No. 08/144,178, filed on Oct. 27, 1993 now U.S. Pat. No. 5,407,937, which is a divisional of application Ser. No. 07/967,630, filed on Oct. 28, 1992, now U.S. Pat. No. 5,272,156, which is a divisional of application Ser. No. 07/732,270, filed on Jul. 18, 1991, issued as U.S. Pat. No. 5,183,827, which is in turn a divisional of application Ser. No. 07/409,476, filed on Sep. 19, 1989, issued as U.S. Pat. No. 5,045,551.

BACKGROUND

This invention relates to novel compounds having retinoid-like activity. More specifically, the invention relates to compounds having an ethynylheteroaromatic acid portion and a second portion which is a 2-substituted tetrahydroquinolinyl, thiochromanyl, or chromanyl group. The acid function may also be converted to an alcohol, aldehyde or ketone or derivatives thereof, or may be reduced to —$CH_3$.

RELATED ART

Carboxylic acid derivatives useful for inhibiting the degeneration of cartilage of the general formula 4-(2-(4,4-dimethyl-6-X)-2-methylvinyl)benzoic acid where X is tetrahydroquinolinyl, chromanyl or thiochromanyl are disclosed in European Patent Application 0133795 published Jan. 9, 1985. See also European Patent Application 176034A published Apr. 2, 1986 where tetrahydronaphthalene compounds having an ethynylbenzoic acid group are disclosed, and U.S. Pat. No. 4,739,098 where three olefinic units from the acid-containing moiety of retinoic acid are replaced by an ethynylphenyl functionality.

SUMMARY OF THE INVENTION

This invention covers compounds of Formula 1

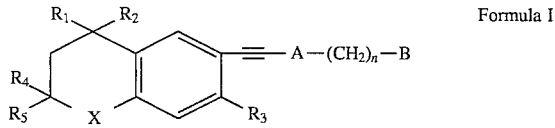

Formula I wherein X is S, O, or NR' where R' is hydrogen or lower alkyl; $R_1$–$R_3$ are hydrogen or lower alkyl, $R_4$ and $R_5$ are hydrogen or lower alkyl with the proviso that $R_4$ and $R_5$ cannot both be hydrogen; A is pyridinyl, thienyl, furyl, pyridazinyl, pyrimidinyl, pyrazinyl, thiazolyl or oxazolyl; n is 0-5; and B is H, —COOH or a pharmaceutically acceptable salt, ester or amide thereof, —$CH_2OH$ or an ether or ester derivative, or —CHO or an acetal derivative, or —$COR_1$ or a ketal derivative where $R_1$ is an alkyl, cycloalkyl or alkenyl group containing 1 to 5 carbons.

In a second aspect, this invention relates to the use of the compounds of Formula 1 for treating dermatoses, such as ache, Darier's disease, psoriasis, icthyosis, eczema, atopic dermatitis and epithelial cancers. These compounds are also useful in the treatment of arthritic diseases and other immunological disorders (e.g. lupus erythematosus), in promoting wound healing, in treating dry eye syndrome and in reversing the effects of sun damage to skin.

This invention also relates to a pharmaceutical formulation comprising a compound of Formula 1 in admixture with a pharmaceutically acceptable excipient.

In another aspect, this invention relates to the process for making a compound of Formula 1 which process comprises reacting a compound of Formula 2 with a compound of Formula III in the presence of cuprous iodide and $Pd(PQ_3)_2Cl_2$ (Q is phenyl) or a similar complex

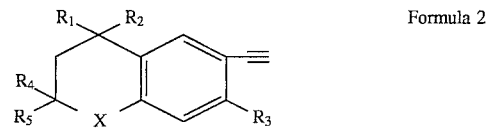

Formula 2

X'—A—$(CH_2)_n$—B    Formula 3 where $R_1$–$R_5$ are the same as described above, X' is a halogen, preferably I; n, and A are the same as defined above; and B is H, or a protected acid, alcohol, aldehyde or ketone, giving the corresponding compound of Formula 1; or to the process of making a compound of Formula 1 which consists of reacting a zinc salt of Formula 4 with a compound of Formula 3 in the presence of $Pd(PQ_3)_4$ (Q is phenyl) or a similar complex.

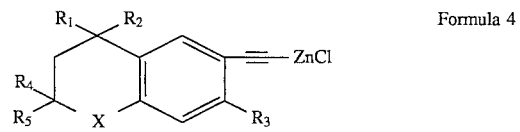

Formula 4 where $R_1$–$R_5$, and X, are the same as defined above, giving the corresponding compound of Formula 1; or homologating a compound of the Formula 5

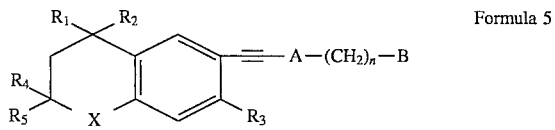

Formula 5 where n is 0-4 to give an acid of Formula 1; or
converting an acid of Formula 1 to a salt; or
forming an acid addition salt;
converting an acid of Formula 1 to an ester; or
converting an acid of Formula 1 to an amide; or
reducing an acid of Formula 1 to an alcohol or aldehyde; or
converting an alcohol of Formula 1 to an ether or ester; or
oxidizing an alcohol of Formula 1 to an aldehyde; or
converting an aldehyde of Formula 1 to an acetal; or
converting a ketone of Formula 1 to a ketal.

GENERAL EMBODIMENTS

Definitions

The term "ester" as used here refers to and covers any compound falling within the definition of that term as classically used in organic chemistry. Where B (of Formula 1) is —COOH, this term covers the products derived from treatment of this function with alcohols. Where the ester is derived from compounds where B is —$CH_2OH$, this term covers compounds of the formula —$CH_2$ OOCR where R is any substituted or unsubstituted aliphatic, aromatic or aliphatic-aromatic group.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids or alcohols. Here, and where ever else used, lower alkyl means having 1–6 carbon atoms. Also preferred are the phenyl or lower alkylphenyl esters.

Amide has the meaning classically accorded that term in organic chemistry. In this instance it includes the unsubstituted amides and all aliphatic and aromatic mono-and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals include the radicals of the formula —CK where K is (—OR)$_2$. Here, R is lower alkyl. Also, K may be —OR$_1$O— where R$_1$ is lower alkyl of 2-5 carbon atoms, straight chain or branched.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of this invention are those where the ethynyl group and the B group are attached to the 2 and 5 positions respectively of a pyridine ring (the 6 and 3 positions in the nicotinic acid nomenclature being equivalent to the 2/5 designation in the pyridine nomenclature) or the 5 and 2 positions respectively of a thiophene group respectively; n is 0; and B is —COOH, an alkali metal salt or organic amine salt, or a lower alkyl ester, or —CH$_2$OH and the lower alkyl esters and ethers thereof, or —CHO and acetal derivatives thereof. The more preferred compounds shown in Formula 6 are: ethyl 6-[(2,2,4,4-tetramethylthiochroman-6-yl)-ethynyl] nicotinate (Compound I, X=S, R$_3$=H, R"=C$_2$H$_5$) 6-[(2,2,4,4-tetramethylthiochroman-6-yl)-ethynyl] nicotinic acid (Compound 2, X=S, R$_3$=H, R"=H) ethyl 6-[(2,2,4,4-tetramethylchroman-6-yl)-ethynyl] nicotinate (Compound 3, X=0, R$_3$=H, R"=C$_2$H$_5$) 6-[(2,2,4,4-tetramethylchroman-6-yl)-ethynyl] nicotinic acid (Compound 4, X=0, R$_3$=H, R"=H) ethyl 6-[(2,2,4,4,7-pentamethylthiochroman-6-yl)-ethynyl] nicotinate (Compound 5, X=S, R$_3$=CH$_3$, R"=C$_2$H$_5$) 6-[(2,2,4,4,7-pentamethylthiochroman-6-yl)-ethynyl] nicotinic acid (Compound 6, X=S, R$_3$=CH$_3$, R"=H) ethyl 6-[(2,2,4,4,7-pentamethylchroman-6-yl)-ethynyl] nicotinate (Compound 7, X=0, R$_3$=CH$_3$, R"=C$_2$H$_5$) 6-[(2,2,4,4,7-pentamethylchroman-6-yl)-ethynyl] nicotinic acid (Compound 8, X=0, R$_3$=CH$_3$, R"=H)

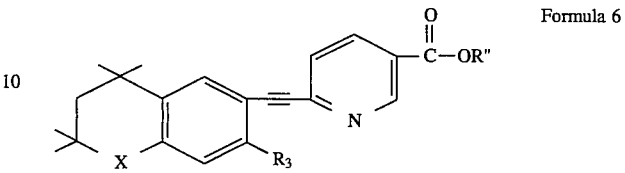

Formula 6

The compounds of this invention may be administered systemically or topically, depending on such considerations as the condition to be treated, need for site-specific treatment, quantity of drug to be administered, and similar considerations.

In the treatment of dermatoses, it will generally be preferred to administer the drug topically, though in certain cases such as treatment of severe cystic ache, oral administration may also be used. Any common topical formulation such as a solution, suspension, gel, ointment, or salve and the like may be used. Preparation of such topical formulations are well described in the art of pharmaceutical formulations as exemplified, for example, *Remington's Pharmaceutical Science*, Edition 17, Mack Publishing Company, Easton, Pa. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intermuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, ache, or other such dermatoses, that a formulation containing between 0.001 and 5 percent by weight, preferably about 0.01 to 1% will usually constitute a therapeutically effective concentration. If administered systemically, an amount between 0.01 and 100 mg per kg body weight per day, but preferably about 0.1 to 10 mg/kg, will effect a therapeutic result in most instances.

The retionic acid like activity of these compounds was confirmed through the classic measure of retionic acid activity involving the effects of retionic acid on ornithine decarboxylase. The original work on the correlation between retionic acid and decrease in cell proliferation was done by Verma & Boutwell, *Cancer Research,* 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-0-tetradecanoyl-phorbol-13-acetate (TPA) induces ODC activity. Retionic acid inhibits this induction of ODC activity by TPA. The compounds of this invention also inhibit TPA induction of ODC as demonstrated by an assay essentially following the procedure set out in *Cancer Res.,* 35: 1662–1670, 1975.

By way of example of retinoic acid-like activity it is noted that in the assay conducted essentially in accordance with the method of Verma & Boutwell, ibid, the following examples of the preferred compounds of the present invention (Compounds 1, 3 and 7) attained an 80% inhibition of TPA induced ODC activity at the following concentrations ($IC_{80}$):

| Compound | $IC_{80}$ conc (nmols) |
|---|---|
| 1 | 0.69 |
| 3 | 0.13 |
| 7 | 0.2 |

SPECIFIC EMBODIMENTS

The compounds of this invention can be made by a number of different synthetic chemical pathways. To illustrate this invention, there is here outlined a series of steps which have been proven to provide the compounds of formula 1 when such synthesis is followed in fact and in spirit. The synthetic chemist will readily appreciate that the conditions set out here are specific embodiments which can be generalized to any and all of the compounds represented by Formula 1. Furthermore, the synthetic chemist will readily appreciate that the herein described synthetic steps may be varied and or adjusted by those skilled in the art without departing from the scope and spirit of the invention.

Compounds of Formula 1 where X is —S— and $R_4$ and $R_5$ are hydrogen or lower alkyl, with the proviso that $R_4$ and $R_5$ both are not hydrogen, are prepared as per Reaction Scheme I

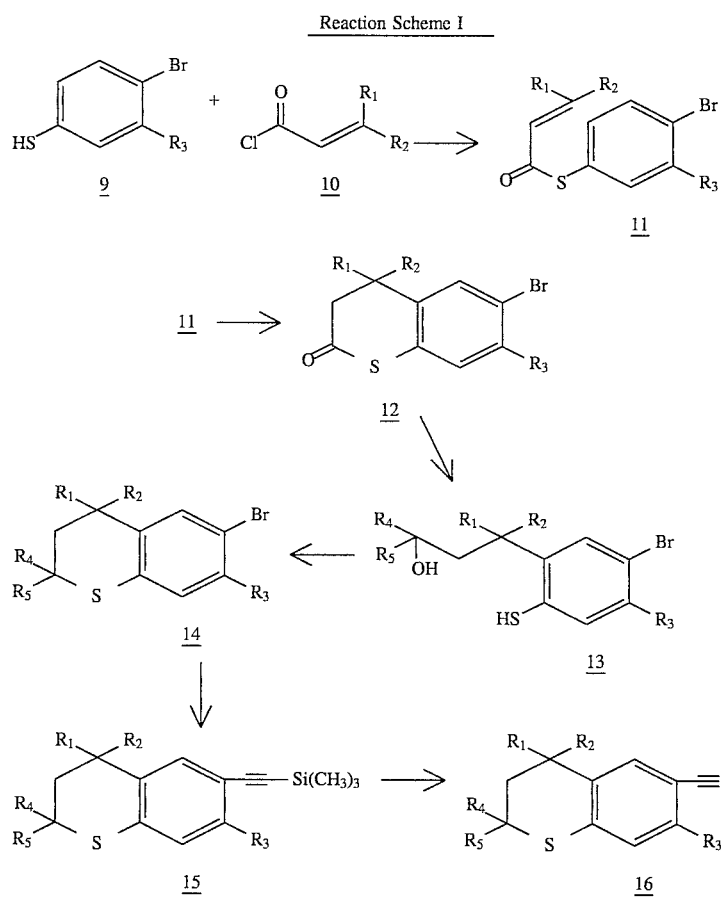

Reaction Scheme I

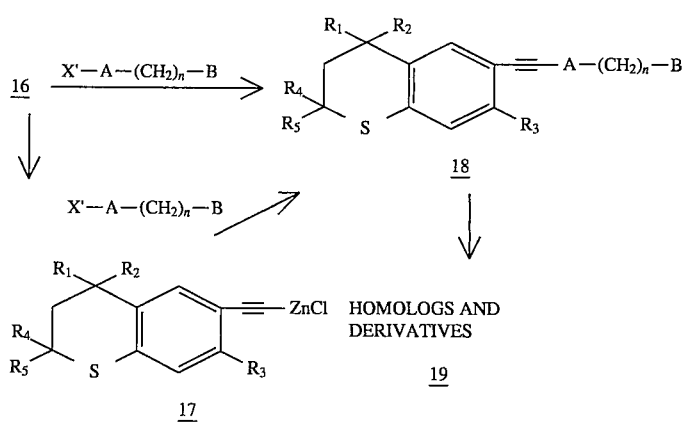

In Reaction Scheme X, $R_1$–$R_3$ are hydrogen or a lower alkyl group, A is as defined above in connection with Formula 1, n is 0-5 and B is H, or a protected acid, alcohol, aldehyde or ketone. X' is Cl, Br or I when n is O but preferably be Br or I when n is 1-5.

Compounds of Formula 1 where X is oxygen and $R_4$ and $R_5$ are hydrogen or lower alkyl, with the proviso that $R_4$ and $R_5$ both are not hydrogen, are prepared as per Reaction Scheme 2.

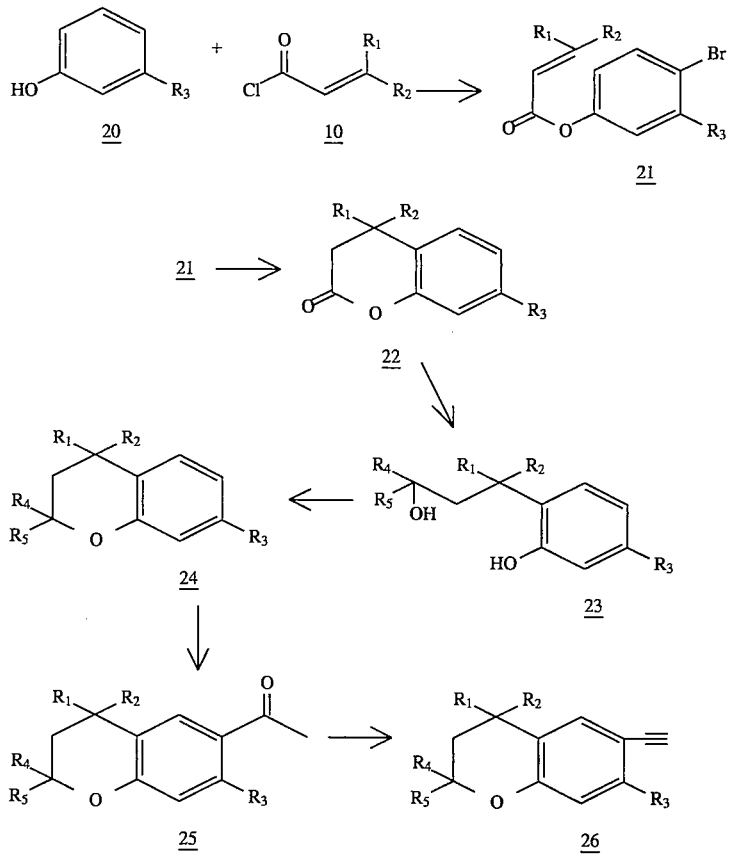

-continued
Reaction Scheme 2

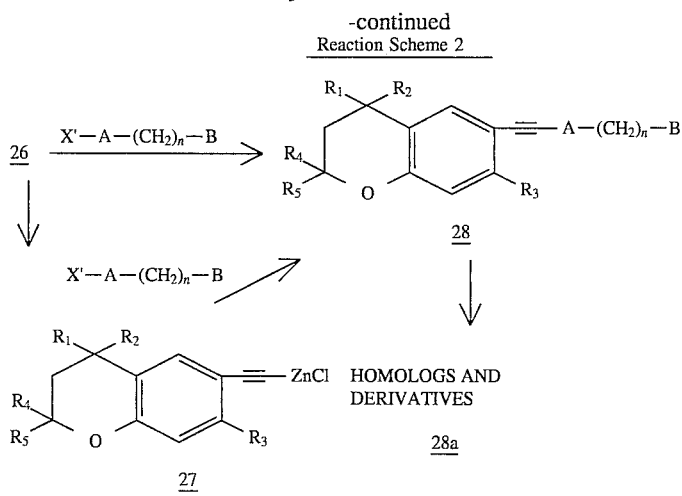

In Reaction Scheme 2 the definitions of $R_1$–$R_5$, n, A, B and X' are the same as in Reaction Scheme 1.

A general description of the synthetic steps outlined in Reaction Schemes 1 and 2 is as follows.

In Reaction Scheme 1 the 4-bromo-thio-phenol (Compound 9) is acylated with an acylating agent, such as an acid chloride (Compound 10) derived from an appropriately substituted acrylic acid. The acylation is conducted in an inert solvent (such as tetrahydrofuran) in the presence of strong base (for example sodium hydrdride). The resulting thioester (Compound 11) which contains the olefinic bond of the acrylic acid moiety is ring closed in the presence of a Fridel Crafts type catalyst (such as aluminum chloride) by stirring in a suitable solvent such as methylene chloride. The resulting 2-oxo-6-bromo-thiochromane (Compound 12) is usually isolated in crystalline form.

The $R_4$ and/or $R_5$ substituents (both of which cannot be hydrogen in accordance with the invention) and which preferably are identical with one another (for example both are methyl) are introduced by treating the 2-oxo-6-bromothiochroman (Compound 12) with a Grignard reagent, bearing the alkyl substituents $R_4$ and $R_5$ (such as methylmagnesium bromide when $R_4$ and $R_5$ are methyl). It will be readily understood by those skilled in the art that depending on the relative molecular ratios of the Grignard reagent and of the oxo-thiochroman compound (compound 12), and also depending on the reaction conditions, the primary products of the reaction may be derivatives where either one or two alkyl groups have been introduced through the Grignard reaction. When the Grignard reagent (such as methylmagnesium bromide) is in excess, the thiochroman ring is opened and the tertiary alcohol derivative of the 4-bromo thiophenol (Compound 13) is formed.

Ring closure of the thiophenol derivative (Compound 13) which has the desired $R_1$, $R_2$, $R_3$, $R_4$ and $R_5$ substituents, is affected by heating in acidic conditions, preferably by heating Compound 13 in aqueous acid. The resulting 6-bromothiochroman which bears the desired alkyl (or hydrogen) substituents, $R_1$, $R_2$, $R_3$, $R_4$ and $R_5$ is shown as Compound 14 in Reaction Scheme 1.

To introduce the acetylene (ethyne) portion into the molecule, the substituted 6-bromothiochroman 14 is reacted with trimethylsilylacetylene in the presence of cuprous iodide and a suitable catalyst, typically having the formula $Pd(PQ_3)_2Cl_2$ (Q is phenyl). The reaction is typically conducted in the presence of bis(triphenylphosphine) palladium (II) chloride catalyst, an acid acceptor, (such as triethylamine) under an inert gas (argon) atmosphere, by heating in a sealed tube. The resulting 6-trimethylsilylethynylthiochroman, is shown as Compound 15 in Reaction Scheme 1.

As is shown on Reaction Scheme 1, the trimethylsilyl moiety is removed from the 6-trimethylsilylethynyl-thiochroman 15 in the next synthetic step, to provide the ring substituted 6-ethynyl-thiochroman derivative (Compound 16). The latter reaction is conducted under basic conditions, preferably under an inert gas atmosphere.

In order to introduce the heteroaryl substituent on the acetylene (ethyne) portion of Compound 16, Compound 16 is coupled with the reagent $X'$-A-$(CH_2)_n$-B (Formula 3) where the symbols X', A and B have the same meaning as defined in connection with Formula 3. In other words, the heteroaryl substituent is introduced into the 6-thiochromanytethyne 16 by reacting the latter with a halogen substituted heteroaromatic compound (Formula 3) in which the heteroaramatic nucleus (A) either has the desired substituent [$(CH_2)n$-B] or wherein the actual substituent $(CH_2)_n$-B can be readily converted to the desired substituent by means of organic reactions well known in the art.

Coupling of the 6-thiochromanylethyne 16 with the reagent $X'$-A-$(CH_2)_n$-B is affected directly in the presence of cuprous iodide, a suitable catalyst, typically of the formula $Pd(PQ_3)_2Cl_2$ and an acid acceptor, such as triethylamine, by heating in a sealed tube under an inert gas (argon) atmosphere.

The resulting disubstituted acetylene compound (Compound 18) may be the target compound made in accordance with the invention, or maybe readily converted into the target compound by such steps as salt formation, esterification, deesterification, homologation, amide formation and the like. These steps are further discussed below.

Compound 18 may also be obtained by first converting the 6-thiochromanylethyne derivative 16 into the corresponding metal salt, such as a zinc salt, (Compound 17) and thereafter coupling the salt 17 with the reagent X'-A-$(CH_2)_n$-B (Formula 3) in the presence of a catalyst having the formula $Pd(PQ_3)_4$ (Q is phenyl), or similar complex.

Derivatization of Compound 18 is indicated in Reaction Scheme 1 as conversion to "homologs and derivatives", Compounds 19.

More specifically with respect to either derivatization or deblocking of protected functionalities in Compound 18, or with respect to the preparation of heteroarometic compounds of the formula X'-A-$(CH_2)_n$-B, (which after coupling either directly yield the compounds of the invention, or are readily converted into them) the following is noted.

Where a protected heteroaromatic compound is needed to couple with the compounds of Formula 2 (Compounds 16 in Reaction Scheme 1), such may be prepared from their corresponding acids, alcohols, ketones or aldehydes. These starting materials, the protected acids, alcohols, aldehydes or ketones, are all available from chemical manufacturers or can be prepared by published methods. Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of n before effecting a coupling reaction, where such compounds are not available from a commercial source, the heteroaromatics where B is —COOH are subjected to homologation by successive treatment under Arndt-Eistert conditions or other homologation procedures. Alternatively, heteroaromatics where B is a different from COOH, may also be homologated by appropriate procedures. The homologated acids can then be esterified by the general procedure outlined in the preceding paragraph.

An alternative means for making compounds where n is 1-5 is to subject the compounds of Formula 1, where B is an acid or other function, to homologation, using the Arndt-Eistert method referred to above, or other homologation procedures.

The acids and salts derived from Formula 1 are readily obtainable from the corresponding esters. Basic saponification with an alkali metal base will provide the acid. For example, an ester of Formula 1 may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert inorganic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexlcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron.* 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds where B is H can be prepared from the corresponding halo-heterocyclic entity, preferably where the halogen is I.

With reference to Reaction Scheme 2, phenol, or a phenol substituted in the 3 (meta) position by an alkyl substituent ($R_3$) (Compound 20) is acylated with an acylating agent, such as an acid chloride (Compound 10) derived from an appropriately substituted acrylic acid. In Reaction Scheme 2, just as in Reaction Scheme 1, the $R_1$ and $R_2$ substituents of the target compounds are introduced through this acrylic acid derivative 10. The acylation with the acid chloride 10 is preferably conducted in the presence of a strong base (e.g. sodium hydride) in an inert solvent (such as tetrahydrofuran). The resulting substituted phenyl-acrylate is shown in Reaction Scheme 2 as Compound 21.

The substituted phenyl-acrylate 21 is ring closed under Friedel Crafts type reaction conditions ($AlCl_3$ catalyst, in an inert solvent, such as methylene chloride) to provide the 2-oxo-chroman compound (Compound 22) which bears, in the 4-position, the $R_1$ and $R_2$ substituents and in the 6-position the $R_3$ substituent (as applicable). Just like the analogous 2-oxo-thiochroman 12 in Reaction Scheme 1, the 2-oxo-chroman 22 of Reaction Scheme 2 is treated with a Grignard reagent to introduce the $R_4$ and $R_5$ substituents. As it was noted out above, $R_4$ and $R_5$ both cannot be hydrogen, and in the preferred embodiments $R_4$ and $R_5$ are identical, for example both are methyl or ethyl. When $R_4$ and $R_5$ are methyl, the Grignard reagent is preferably methylmagnesium chloride (dissolved in tetrahydrofuran, THF). A solution of Compound 22 in a suitable solvent, for example in dry diethylether is added to this Grignard reagent. The resulting phenol containing a tertiary alcohol side chain, (that is a molecule in which the chroman ring had been opened) is shown in Reaction Scheme 2 as Compound 23.

Compound 23 which already has the desired $R_1$, $R_2$, $R_3$, $R_4$ and $R_5$ substituents, is ring closed under acidic conditions, (e.g. by heating in aqueous sulfuric acid) to provide the chromane derivative (Compound 24). It should be noted that up to this point in the synthetic sequence (which is preferably but not necessarily exclusively used for making the compounds of the invention) similar or analogous steps are involved for making both the thiochroman (Reaction scheme 1) and chroman derivatives (Reaction Scheme 2), the only difference being that in Reaction Scheme 2 the starting phenol derivative does not have a halogen (such as a bromo) substituent.

Because of the lack of the halogen substituent in the preferred synthetic sequence for preparing the chroman compounds of the invention, the preferred and herein illustrated steps (Reaction Scheme 2) for introducing the acetylene (ethyne) group into the 6-position of the chroman moiety are different from the steps utilized for introducing the acetylene moiety into the analogous thiochroman (Reaction Scheme 1).

Thus, in Reaction Scheme 2 an acetyl group is introduced into the 6-position of the chroman derivative 24 under Friedel Crafts type conditions. This acetylation is preferably conducted with acetyl chloride, in nitromethane solvent, in the presence of aluminum chloride. The resulting 6-acetyl-chroman derivative is Compound 25.

The acetylenic (triple) bond is introduced into the molecule by converting the 6-acetyl moiety of chroman 25 to an acetylene moiety. This is accomplished, preferably, by treatment with lithium diisopropylamide (at low temperature, such as −78 degrees C.) which causes enolization of the acetyl group. The intermediate enol compound (not shown in Reaction Scheme 2) is esterified by treatment-with diethylchlorophosphate (or the like) and is again reacted at reduced temperature (e.g. −78 degrees C.) with lithium diisopropylamide, to form the triple bond (presumably by an elimination reaction) and to yield the 6-ethynyl-chroman derivative (Compound 26).

It is noted at this point that the present invention is not intended to be limited or bound by the above-mentioned and other theories of reaction mechanisms. Brief description of theory of reaction mechanisms (where applicable) are given to further enable and facilitate the work of a skilled artisan in the field to modify and adjust the synthetic conditions to fit particular specific intermediates and to make the several compounds of the invention, without departing from the scope and spirit of the invention.

Referring back again to Reaction Scheme 2, the 6-ethynyl-chroman derivative 26 may be converted into the target compounds of the invention in synthetic steps which are analogous to the conversion of 6-ethynyl-thiochromans (Compound 16) into the corresponding target thiochroman derivatives (See Reaction Scheme 1). Briefly, Compound 26 is preferably heated with a reagent X'-A-$(CH_2)_n$-B (Formula 3) in the presence of cuprous iodide, a suitable catalyst, typically of the formula $Pd(PQ_3)_2 Cl_2$ (Q is phenyl or the like) and an acid acceptor, such as triethylamine. This coupling reaction, yields the target chroman compounds, (Compound 28) or such derivatives which are readily converted into the target compounds by protection, deprotection esterification, homologation etc., as is discussed in connectin with Reaction Scheme 1. The homologs are indicated, as a group, as Compound 28a in Reaction Scheme 2.

Alternatively, the 6-ethynyl-chroman compounds 26 may first be converted to the corresponding metal (zinc) salt (Compound 27) and thereafter coupled with the reagent X'-A-$(CH_2)_n$-B (Formula 3) under conditions which are similar to the conditions described in Reaction Scheme 1 for coupling of Compounds 18 with the same reagent.

The compounds of the invention where $X=NR^1$ ($R^1$ is H or lower alkyl) can be made, for example, in a synthetic sequence which is analogous to the sequences described in the sequences described in Reaction Schemes 1 and 2, but starting with an appropriately substituted aniline derivative instead of a thiophenol or phenol.

The following examples of specific compounds of the invention, and specific examples of the synthetic steps in which the compounds and certain intermediates are made, are set out to illustrate the invention, not to limit its scope.

Specific Examples

Ethyl 6-chloronicotinate (Compound 29)

A mixture of 15.75 g (0.1 mol) 6-chloronicotinic acid, 6.9 g (0.15 mol) ethanol, 22.7 g (0.11 mol) dicyclohexylcarbodiimide and 3.7 g dimethylaminopyridine in 200 ml methylene chloride was heated at reflux for 2 hours. The mixture was allowed to cool, solvent removed in vacuo and residue subjected to flash chromatography to give the title compound as a low-melting white solid. PMR (CDCl$_3$): & 1.44 (3H, t, J-6.2 Hz) 4.44 (2H, q, J-4.4 Hz), 7.44-(1H, d, J-8.1 Hz), 8.27 (1H, dd, J-8.1 Hz, 3 Hz), 9.02 (1H, d, J-3 Hz).

The foregoing procedure may be used to esterify any of the other halo-substituted acids employed in the making of these compounds such as:
ethyl 2-(2-chloropyrid-5-yl)acetate;
ethyl 5-(2-chloropyrid-5-yl)pentanoate;
ethyl 2-(2-iodofur-5-yl)acetate;
ethyl 5-(2-iodofur-5-yl)pentanoate;
ethyl 2-(2-iodothien-5-yl)acetate;
ethyl 5-(2-iodothien-5-yl)pentanoate;
ethyl 2-(3-chloropyridazin-6-yl)acetate;
ethyl 5-(3-chloropyridazin-6-yl)pentanoate; and the corresponding chloro, or other halo, substituted pyrimidinyl or pyrazinyl analogues of such esters. The just mentioned esters (including ethyl-6-chloronicotinate, Compound 29) can serve as the reagents, $X^1$-A-$(CH_2)_n$-B for coupling with the correspoding ethynyl compounds (such as Compounds 16 and 26, or their zinc salts 17 and 27) to provide the target compounds of the invention.

S-(4-bromopenyl) 3,3-dimethylthioacrylate (Compound 30)

To an ice bath cooled solution of 1.92 g (80 mmol) of NaH (obtained from a 60% suspension in mineral oil by 3×15 ml hexane wash) in 30 ml of dry THF was added slowly under argon a solution of 15.1 g (80 mmol) of 4-bromothiophenol in 60 ml of dry THF over 1 h. The mixture was stirred at 0 degrees C. for a further 30 min and then treated with a solution of 10.1 g (85 mmol) of dimethylacryloyl chloride in 30 ml of dry THF. The cooling bath was then removed and the mixture then stirred at room temperature for 40 h. The reaction mixture was poured into 200 ml of water containing 2 ml of glacial acetic acid and the organic layer was separated. The organic layer was washed with 2×75 ml of water and then dried (MgSO$_4$). The solvent was removed in vacuo to give the title compound as a yellow oil. PMR (CDCl$_3$): & 1.91 (3H, s), 2.14 (3H, s), 6.03-6.06 (1H, m), 7.28 (2H, d, J-8.6 Hz), 7.53 (2H, d, J-8.6 Hz).

4,4,-Dimethyl-6-bromo-2-oxo-thiochroman (Compound 31)

To a stirred, ice-cooled suspension of 15.9 g (119 mmol) of aluminum chloride in 140 ml of methylene chloride was added under nitrogen a solution of 21.64 g (79.9 mmol) of S-(4-bromophenyl) 3,3-dimethyl-thioacrylate (Compound 30) in 100 ml of methylene chloride. The mixture was then stirred at room temperature for 72 h and then poured into 250 g of an ice and brine mixture. The mixture was extracted with methylene chloride and the combined organic extracts were washed with saturated NaCl solution and then dried (MgSO$_4$). The solvent was removed in vacuo and the residue recrystaliized from hexanes to give the title compound as white crystals. PMR (CDCl$_3$): & 1.40 (6H, s), 2.67 (2H, s), 7.31-7.4.0 (3H, m). MS exact mass, m/e 269.9714 (calcd. for C$_{11}$H$_{11}$ SOBr, 269.9714).

4-Bromo-2-(1,1,3-trimethyl-3-hydroxybutyl) thiophenol (Compound 32)

To 3.49 g (32.8 mmol) of lithium perchlorate was added under argon 35 ml of 3.0M (105 mmol) methyl magnesium bromide in ether. The above mixture was treated dropwise with stirring with a solution of 2.961 g (10.926 mmol) of 4,4-dimethyl-6-bromo-2-oxo-thiochroman (Compound 31) and the reaction mixture was then heated at reflux for 70 h. The reaction mixture was then allowed to cool and poured onto a mixture of 100 g of ice and 8 ml of conc. H$_2$SO$_4$. The organic layer was separated and the aqueous layer was extracted with 2×25 ml of ether. The organic layers were combined and washed successively with 2×25 ml of saturated NaHCO$_3$ solution, 25 ml of water and 25 ml of saturated NaCl solution and then dried (MgSO$_4$). The solvent was removed in-vacuo and the residue purified by flash chromatography to give the title compound as a pale yellow oil. PMR (CDCl$_3$): & 1.05 (6H, s), 1.52 (6H, s), 2.30 (2H, s), 3.71 (1H, s), 7.22 (1H, dd, J-8.5 Hz, 2.1 Hz), 7.28 (1H, d, J-8.5 Hz), 7.35 (1H, d, J-2.1 Hz)

Using ethyl magnesium bromide, instead of methyl magnesium bromide, provides the corresponding 4-bromo-2-(1,1 dimethyl 3-ethyl-3-hydroxypentyl)-thiophenol.

2,2,4,4-Tetramethyl-6-bromothiochroman (Compound 33)

A mixture of 500 mg (1.49 mmol) of 4-bromo-2-(1,1,3-trimethyl-3-hydroxybutyl) thiophenol (Compound 32) and 8 ml of 20 percent aqueous H$_2$SO$_4$ was heated at reflux for 24 h. The mixture was extracted with hexanes, the organic extracts were combined and washed successively with water, saturated NaHCO$_3$, water again, saturated NaCl and then dried (MgSO$_4$). The solvent was removed in vacuo and the residue purified by flash chromatography (silica; hexanes) to give the title compound as a colorless oil. PMR (CDCl$_3$): & 1.35 (6H, s), 1.40 (6H, s), 1.93 (2H, s), 7.17 (1H, dd, J-8.4 Hz, 2.1 Hz), 7.23 (1H, d, J-8.4 Hz), 7.26 (1H, d, J-2.1 Hz). MS exact mass, m/e 284.0221 (calcd. for C$_{13}$H$_{17}$ S Br, 284.0234).

2,2,4,4-Tetramethyl-6-trimethylsilylethynyl-thiochroman (Compound 34)

A solution of 600 mg (2.11 mmol) of 2,2,4,4-tetramethyl-6-bromothiochroman (Compound 33) in 1.5 ml of triethylamine was placed in a heavy-walled tube and degassed and then treated under argon with 1.4 g (14.3 mmol) of trimethylsilylacetylene and a powdered mixture of 75 mg (0.39 mmol) of cuprous iodide and 150 mg (0.21 mmol) of bis(triphenylphosphine) palladium (II) chloridel. The reaction mixture was degassed again, then placed under argon and the tube was sealed. The mixture was heated at 100 degrees C. for 24 h, allowed to cool to room temperature and then treated with a further 1.4 g (14.3 mmol) of trimethylsilylacetylene and a powdered mixture of 75 mg (0.39 mmol) of cuprous iodide and 150 mg (0.21 mmol) of bis(triphenylphosphine) palladium (II) chloride. The mixture was then degassed, placed under argon and then heated in the sealed tube at 100 degrees C. for 96 h. The mixture was cooled to room temperature and extracted with 3×10 ml of ether. The organic extracts were combined, washed successively with 25 ml of water and 25 ml of saturated sodium chloride solution and then dried (MgSO$_4$). The solvent was removed in vacuo and the residue purified by flash chromatography (silica; hexanes followed by 3% ethyl acetate in hexanes) to give the title compound as a yellow, crystalline solid. PMR (CDCl$_3$): & 0.23 (9H, s) , 1.36 (6H, s), 1.39 (6H, s), 1.94 (2H, s), 7.17 (1H, dd, J-8.2 Hz, 1.8 Hz), 7.25 (1H, d, J-1.8 Hz), 7.30 (1H, d, J-8.2 Hz). MS exact mass, m/l 302.1519 (calcd. for C$_{18}$H$_{26}$ S Si, 382.1524).

2,2,4,4-Tetramethyl-6-ethynylthiochroman (Compound 35)

To a solution of 527.6 mg (1.75 mmol) of 2,2,4,4-tetramethyl-6-trimethylsilyl-ethynylthiochroman (Compound 34) in 4 ml of isopropanol was added, under argon, 4 ml of 1N KOH solution. The reaction mixture was stirred at room temperature for 20 h and the isopropanol was then removed under vacuum. The residue was extracted with ether and the combined ether extracts were washed successively with water and saturated NaCl solution and then dried (MgSO$_4$). The solvent was removed in vacuo to give the title compound as a yellow oil. PMR (CDCl$_3$): & 1.34 (6H, s), 1.37 (6H, s), 1.91 (2H, s), 2.99 (1H, s), 7.17 (1H, dd, J-8.1 Hz, 1.8 Hz), 7.26 (1H, d, J-1.8 Hz), 7.30 (1H, d, J-S.1 Hz). MS exact mass, m/e 230.1122 (calcd. for C$_{15}$H$_{18}$S, 230.1129)

Ethyl 6-[(2,2,4,4-tetramethyl-thiochroman-6-yl)-ethynyl]-nicotinate (Compound 1)

A solution of 232 mg (1.01 mmol) of 2,2,4,4-tetramethyl-6-ethynylthiochroman (Compound 35) and 190 mg (1.03 mmol) of ethyl 6-chloro-nicotinate (Compound 29) in 2 ml of triethylamine was placed in a heavy-walled glass tube, degassed, placed under argon and then treated with a powdered mixture of 53 mg (0.28 mmol) of cuprous iodide and 84 mg (0.12 mmol) of bis(triphenylphosphine) palladium (II) chloride. The mixture was degassed again, placed under argon and the tube was sealed. The reaction mixture was heated at 55 degrees C. for 60 h and then cooled to room temperature. The mixture was treated with water and ether and the organic layer was separated. The aqueous layer was extracted with ether, the organic layers were then combined and washed with saturated NaCl solution and then dried (MgSO$_4$). The solvent was removed in vacuo and the resultant residue was purified by flash chromatograhy (silica; 10% ethyl acetate in hexanes) to give the title compound as a dark yellow oil. PMR (CDCl$_3$): & 1.32-1.43 (15H, m), 1.92 (2H, s), 4.38 (2H, q, J-7.1 Hz), 7.28 (1H, dd, J-8.3 Hz, 1.8 Hz), 7.32-7.38 (2H, m), 7.53 (1H, d, J-8.3 Hz), 8.24 (1H, dd, J-8.2 Hz, 2.2 Hz), 9.16 (1H, d, J-2.2 Hz). MS exact mass, m/e 379.1594 (calcd. for C$_{23}$ H$_{25}$ NO$_2$S, 379.1606).

Using the method for the preparation of Compound 1, but substituting the appropriate ethynylthiochroman (Compound 16 in Reaction Scheme 1) and the appropriate halo substituted heteroaromatic ester (Formula 3, prepared for example as specifically described for Compound 29) the following compounds of the invention may be prepared:

ethyl 6-[(2,2,4,4,7-pentamethylthiochroman-6-yl)ethynyl]nicotinate;
ethyl 6-[(2,2,4,4-tetramethyl-7-ethylthiochroman-6-yl)ethynyl]nicotinate;
ethyl 6-[(2,2,4,4-tetramethyl-7-propylthiochroman-6-yl)ethynyl]nicotinate;
ethyl 6-[(2,2,4,4-tetramethyl-7-hexylthiochroman-6-yl)ethynyl]nicotinate;
ethyl [((2,2,4,4-tetramethylthiochroman-6-yl)ethynyl)pyrid-5-yl]acetate;
ethyl [((2,2,4,4,7-pentamethylthiochroman-6-yl)ethynyl)pyrid-5-yl]acetate;
ethyl [((2,2,4,4-tetramethyl-7-ethylthiochroman-6-yl)ethynyl)pyrid-5-yl]acetate;
ethyl [((2,2,4,4-tetramethyl-7-hexylthiochroman-6-yl)ethynyl)pyrid-5-yl]acetate;
ethyl 3-[((2,2,4,4-tetramethylthiochroman-2-yl)ethynyl)pyrid-5-yl]propionate;
ethyl 3-[((2,2,4,4,7-pentamethylthiochroman-6-yl)ethynyl)pyrid-5-yl]propionate;
ethyl 3-[((2,2,4,4-tetramethyl-7-ethylthiochroman-6-yl)ethynyl)pyrid-5-yl]propionate;
ethyl 3-[(2,2,4,4-tetramethyl-7-hexylthiochroman-6-yl)ethynyl)pyrid-5-yl]propionate;
ethyl 5-[((2,2,4,4-tetramethylthiochroman-6-yl)-ethynyl)pyrid-5-yl]pentanoate;
ethyl 5-[((2,2,4,4,7-pentamethylthiochroman-6-yl)ethynyl)pyrid-5-yl]pentanoate;
ethyl 5-[((2,2,4,4-tetramethyl-7-ethylthiochroman-6-yl)ethynyl)pyrid-5-yl]pentanoate;
ethyl [5-((2,2,4,4-tetramethylthiochroman-6-yl)ethynyl)fur-2-yl]acetate;
ethyl [5-((2,2,4,4,7-pentamethylthiochroman-6-yl)ethynyl)fur- 2-yl]acetate;
ethyl [5-((2,2,4,4,-tetramethyl-7-ethylthiochroman-6-yl)ethynyl)fur-2-yl]acetate;
ethyl [5-((2,2,4,4-tetramethyl-7-hexylthiochroman-6-yl)ethynyl)fur-2-yl]acetate;
ethyl 5-[((2,2,4,4-tetramethylthiochroman-6-yl)ethynyl)fur2-yl]pentanoate;
ethyl 5-[5((2,2,4,4,7-pentamethylthiochroman-6-yl)ethynyl)-fur-2-yl]pentanoate;
ethyl 5-[5-((2,2,4,4-tetramethyl-7-ethylthiochroman-6-yl)ethynyl)fur-2-yl]pentanoate;
ethyl 5-[5-((2,2,4,4-tetramethyl-7-hexylthiochroman-6-yl)ethynyl)fur-2-yl]pentanoate;
ethyl [5-((2,2,4,4-tetramethylthiochroman-6-yl)ethynyl)thien-2-yl]acetate;
ethyl [5-((2,2,4,4,7-pentamethylthiochroman-6-yl)ethynyl)thien-2-yl]acetate;
ethyl [5-((2,2,4,4-tetramethyl-7-ethylthiochroman-6-yl)ethynyl)thien-2-yl]acetate;
ethyl [5-((2,2,4,4-tetramethyl-7-hexylthiochroman-6-yl)ethynyl)thien-2-yl]acetate;
ethyl 5-[5-2,2,4,4-tetramethylthiochroman-6-yl)ethynyl)thien-2-yl]pentanoate;
ethyl 5-[5-((2,2,4,4,7-pentamethylthiochroman-6-yl)ethynyl)thien-2-yl]pentanoate;
ethyl 5-[5-((2,2,4,4-tetramethyl-7-ethylthiochroman-6-yl)ethynyl)thien-2-yl]pentanoate;
ethyl 5-[5-((2,2,4,4-tetramethyl-7-hexylthiochroman-6-yl)ethynyl)thien-2-yl]pentanoate;
ethyl [6-((2,2,4,4-tetramethylthiochroman-6-yl)ethynyl)-pyridazin-3-yl]acetate;
ethyl [6((2,2,4,4,7-pentamethylthiochroman-6-yl)ethynyl)pyridazin-3-yl]acetate;
ethyl [6-((2,2,4,4-tetramethyl-7-ethylthiochroman-6-yl)ethynyl)pyridazin-3-yl]acetate;
ethyl [6-((2,2,4,4-tetramethyl-7-hexylthiochroman-6-yl)ethynyl)pyridazin-3-yl]acetate;
ethyl-5-[6((2,2,4,4-tetramethylthiochroman-6-yl)ethynyl)-pyridazin-3-yl]pentanoate;
ethyl 5-[6-((2,2,4,4,7-pentamethylthiochroman-6-yl)ethynyl)pyridazin-3-yl]pentanoate;
ethyl 5-[6-((2,2,4,4-tetramethyl-7-ethylthiochroman-6 -yl)ethynyl)pyridazin-3-yl]pentanoate;
ethyl 5-[6-((2,2,4,4-tetramethyl-7-hexylthiochroman-6-yl)ethynyl)pyridazin-3-yl]pentanoate;
ethyl [5-((2,2,4,4-tetramethylthiochroman-6-yl)ethynyl)-pyrimidin-2-yl]acetate;
ethyl [5-((2,2,4,4,7-pentamethylthiochroman-6-yl)ethynyl)-pyrimidin-2-yl]acetate;
ethyl [5-((2,2,4,4-tetramethyl-7-ethylthiochroman-6-yl)ethynyl)pyrimidin-2-yl]acetate;
ethyl [5-((2,2,4,4-tetramethyl-7-hexylthiochroman-6-yl)ethynyl)pyrimidin-2-yl]acetate;
ethyl 5-[5-(2,2,4,4-tetramethylthiochroman-6-yl)ethynyl)pyrimidin-2-yl]pentanoate;
ethyl 5-[5-((2,2,4,4,7-pentamethylthiochroman-6-yl)ethynyl)pyrimidin-2-yl]pentanoate;
ethyl 5-[5-((2,2,4,4-tetramethyl-7-ethylthiochroman-6-yl)ethynyl)pyrimidin-2-yl]pentanoate;
ethyl 5-[5-((2,2,4,4-tetramethyl-7-hexylthiochroman-6-yl)ethynyl)pyrimidin-2-yl]pentanoate;
ethyl [5-((2,2,4,4-tetramethylthiochroman-6-yl)ethynyl)-pyrazin- 2-yl]acetate;
ethyl [5-((2,2,4,4,7-pentamethylthiochroman-6-yl)ethynyl)pyrazin-2-yl]acetate;
ethyl [5-((2,2,4,4-tetramethyl-7-ethylthiochroman-6-yl)ethynyl)pyrazin-2-yl]acetate;
ethyl [5-((2,2,4,4-tetramethyl-7-hexylthiochroman-6-yl)ethynyl)pyrazin-2-yl]acetate;
ethyl 5-[5-((2,2,4,4-tetramethylthiochroman-6-yl)ethynyl)-pyrazin-2-yl]pentanoate;
ethyl 5-[5-((2,2,4,4,7-pentamethylthiochroman-6-yl)ethynyl)pyrazin-2-yl]pentanoate;
ethyl 5-[5-((2,2,4,4-tetramethyl-7-ethylthiochroman-6-yl)ethynyl)pyrazin-2-yl]pentanoate;
ethyl 5-[5-((2,2,4,4-tetramethyl-7-hexylthiochroman-6-yl)ethynyl)pyrazin-2-yl]pentanoate;
ethyl 6-[(2,2-diethyl-4,4-dimethylthiochroman-6-yl)ethynyl]nicotinate; and
ethyl 6-[2,2-diethyl-4,4,7-trimethylthiochroman-6-yl)ethynyl]nicotinate.

Phenyl 3,3-dimethylacrylate (Compound 37)

To an ice bath cooled solution of 1.29 g (54 mmol) of NaH (obtained from a 60% suspension in mineral oil by 3×10 ml hexane wash) in 20 ml of dry THF was added slowly under oxygen a solution of 5 g (53 mmol) of phenol in 50 ml of dry THF. The mixture was then treated with a solution of 7 g (59 mmol) of dimethylacryloyl chloride in 30 ml of dry THF. The cooling bath was then removed and the mixture was stirred for a further 2.5 h. The reaction mixture was then poured into 150 ml of water containing 1 ml of glacial acetic acid. The mixture was extracted with 150 ml ether and the ether extract washed with saturated NaCl solution and then dried (MgSO$_4$). The solvent was removed in vacuo and the residue purified by flash chromatography (silica; 5% ether in hexanes) to give the title compound as a yellow oil. PMR (CDCl$_3$)): & 1.99 (3H, s), 2.24 (3H, s), 5.93 (1H, broad s), 7.10 (2H, d, J-7.8 Hz) 7.22 (1H, t, J-7.8 Hz), 7.38 (2H, t, J-7.8 Hz).

4,4-Dimethyl-2-oxo-chroman (Compound 38)

To a stirred, ice-cooled suspension of 10.4 g (78 mmol) of aluminum chloride in 160 ml of methylene chloride was added slowly under argon a solution of 7 g (39.8 mmol) of phenyl 3,3-dimethylacrylate (Compound 37) in 40 ml of methylene chloride. The cooling bath was removed and the mixture stirred for a further 42 h. The mixture was poured into a mixture of ice and brine and the organic layer separated. The aqueous layer was extracted with methylene chloride and the organic extracts were combined and washed with saturated NaCl solution and then dried ($MgSO_4$). The solvent was removed in vacuo and the residue purified by flash chromatography (silica; 10% ether in hexane) to give the title compound as a colorless oil. PMR ($CDCl_3$): & 1.30 (6H, s), 2.56 (2H, s) , 7.06 (1H, dd, J-8.0 Hz, 1.4 Hz), 7.16 (1H, td, J-8.0 Hz, 1.4 Hz), 7.26 (1H, td, J-S.0 Hz, 1.7 Hz), 7.33 (1H, dd, J-8.0 Hz, 1.7 Hz). MS exact mass, m/e 176.0852 (calcd. for $C_{11}H_{12}O_2$, 176.0837.

2-(1,1,3-Trimethyl-3-hydroxybutyl)phenol (Compound 39)

To 11 ml of 3.0M (33 mmol) methyl magnesium chloride in THF, cooled in an ice bath, was added, under nitrogen, a solution of 1.96 g (11.1 mmol) of 4,4-dimethyl-2-oxo-chroman (Compound 38) in 35 ml of dry ether. The cooling bath was then removed and the mixture stirred at room temperature for 72 h. The reaction mixture was then poured onto a mixture of 100 g of ice and 3 ml of conc. $H_2SO_4$ and stirred until the magnesium salts were dissolved. The organic layer was separated and the aqueous layer extracted with 2×50 ml of ether. The organic layers were combined and washed successively with water, saturated $NaHCO_3$ and saturated NaCl solutions and then dried ($MgSO_4$). The solvent was removed in vacuo and the residue was purified by flash chromatography (silica; 20% ethyl acetate in hexanes) to give the title compound as a pale yellow solid. PMR ($CDCl_3$): & 1.13 (6H, s), 1.48 (6H, s), 1.89 (1H, s), 2.23 (2H, s), 6.60 (1H, dd, J-7.9 Hz, 1.4 Hz), 6.83 (1H, s), 6.84 (1H, td, J-7.9 Hz, 1.4 Hz), 7.07 (1H, td, J-7.9 Hz, 1.6 Hz), 7.31 (1H, dd, J-7.9 Hz, 1.6 Hz). MS exact mass, m/e 208.1458 (calcd. for $C_{13}H_{20}O_2$, 208.1464).

2,2,4,4-Tetramethyl-chroman (Compound 40)

A mixture of 2.98 g (14.3 mmol) of 2-(1,1,3-trimethyl-3-hydroxybutyl) phenol (Compound 39) and 40 ml of 20% aqueous $H_2SO_4$ was heated at reflux, under nitrogen, for 4 h. The mixture was stirred at room temperature for a further 72 h and then diluted with 50 ml of water. The mixture was extracted with 3×20 ml of hexanes. The organic extracts were then combined and washed successively with water and saturated NaCl solution and then dried ($MgSO_4$). The solvent was then removed in vacuo to give the title compound as a colorless oil. PMR ($CDCl_3$): & 1.36 (dH, s), 1.37 (dH, s), 1.83 (2H, s), 6.71 (1H, dd, J-8.2 Hz, 1.5 Hz) 6.92 (1H, td, J-8.2 Hz, 1.5 Hz), 7.09 (1H, td, J-8.2 Hz, 1.5 Hz), 7.29 (1H, dd, J-8.2 Hz, 1.5 Hz).

2,2,4,4-Tetramethyl-6-acetyl-chroman (Compound 41)

To an ice bath cooled solution of 2 g (10.53 mmol) of 2,2,4,4-tetramethylchroman (Compound 40) in 25 ml of nitromethane was added, under nitrogen, 941 mg (11.99 mmol) of acetyl chloride followed by 1.59 g (11.92 mmol) of aluminum chloride. The cooling bath was then removed and the mixture stirred at room temperature for 16 h. The mixture was then cooled again in an ice bath and treated with 25 ml of conc. HCl. The mixture was then filtered and the residue washed with methylene chloride. The filtrate was concentrated in vacuo and the resultant residue was purified by flash chromatography (silica; 10% ethyl acetate in hexanes) to give the title compound as a yellow oil. PMR ($CDCl_3$): & 1.38 (6H, s), 1.39 (6H, s), 1.87 (2H, s), 2.56 (3H, s), 6.83 (1H, d, J-8.7 Hz), 7.71 (1H, dd, J-8.7 Hz, 2.1 Hz), 7.98 (1H, d, J-2.1 Hz). MS exact mass, m/e 232.1468 (calcd. for $C_{13}H_{20}O_2$, 232.1464).

2,2,4,4-Tetramethyl-6-ethynyl-chroman (Compound 42)

To a cooled (−78 degrees C.) solution of 522 mg (5.17 mmol) of diisopropylamine in 8 ml of dry THF was added slowly, under nitrogen, 3.23 ml of 1.6M (5.17 mmol) n-butyl lithium in hexane. The mixture was stirred at −78 degrees C. for 40 minutes and then treated with a solution of 1.24 g (5.17 mmol) of 2,2,4,4-tetramethyl-6-acetylchroman (Compound 41) in 2 ml of dry THF. The mixture was stirred at −78 degrees C. for a further 1 h and then treated with 895 mg (5.19 mmol) of diethylchlorophosphate. The reaction mixture was allowed to warm to room temperature and transferred by double-ended needle into a solution of lithium diisopropylamide in THF at −78 degrees C. [prepared as described above from 1.04 g (10.34 mmol) of diisopropylamine and 6.46 ml of 1.6M (10.34 mmol) n-butyl lithium in hexane]. The cooling bath was removed and the mixture was stirred at room temperature for 16 h. The mixture was then treated with 10 ml of ice water and acidified to a pH of 2 with 10% HCl. The organic layer was separated and the aqueous layer was extracted with 3×30 ml of pentane. The organic extracts were combined and washed successively with 2×30 ml of dilute HCl, water, 3×30 ml of saturated $NaHCO_3$ solution and saturated NaCl solution and then dried ($MgSO_4$). The solvent was removed in vacuo and the residue was purified by flash chromatography (silica; 2% ethyl acetate in hexane) to give the title compound as a pale yellow oil. PMR ($CDCl_3$): & 1.31 (6H, s), 1.32 (6H, s), 1.50 (2H, s), 3.00 (1H, s), 6.72 (1H, d, J-S.4 Hz), 7.20 (1H, dd, J-8.4 Hz, 2.1 Hz), 7.42 (1H, d, J-2.1 Hz). MS exact mass, m/e 214.1251 (calcd. for $C_{15}H_{18}O$, 214.1357).

Ethyl 6-[(2,2,4,4-tetramethylchroman-6-yl)-ethynyl]nicotinate (Compound 3)

A solution of 233 mg (1.09 mmol) of 2,2,4,4-tetramethyl-6-ethynylchroman (Compound 42) and 209 mg (1.09 mmol) of ethyl 6-chloronicotinate (Compound 29) in 1 ml of triethylamine was degassed and then treated under argon with a powdered mixture of 50 mg (0.26 mmol) of cuprous iodide and 100 mg (0.14 mmol) of bis(triphenylphosphine) palladium (II) chloride. The reaction mixture was heated under argon at 55 degrees C. for 80 h and then cooled to room temperature. The triethylamine was then removed under vacuum and the residue purified by flash chromatography (silica; 5% ethyl acetate in hexanes) to give the title compound as a yellow oil. PMR ($CDCl_3$): & 1.36 (12H, s), 1.42 (3H, t, J-7.2 Hz), 1.85 (2H, s), 4.37 (2H, q, J-7.2 Hz), 6.79 (1H, d, J-7.4 Hz), 7.34 (1H, dd, J-8.4 Hz, 2.1 Hz), 7.56 (1H, d, J-8.7 Hz), 7.60 (1H, d, J-2.1 Hz), 8.27 (1H, dd, J-8.7 Hz, 2.4 Hz), 9.19 (1H, d, J-2.4 Hz). MS exact masss, m/e 363.1837 (calcd. for $C_{23}H_{25}O_3N$, 363.1834).

3-Methyl-phenyl-3,3-dimethylacrylate (Compound 44)

A 60% suspension of sodium hydride (3.22 g; 81 mmol) in mineral oil was washed with 3×10 ml of hexane and then treated with 30 ml of dry THF. This mixture was cooled in an ice-bath and then treated with a solution of 8.6 g (79.5 mmol) of m-cresol in 80 ml of dry THF. The reaction mixture was stirred for 10 min and then treated with a solution of 10.5 g (88.5 mmol) of dimethylacryloyl chloride in 40 ml of dry THF. The reaction mixture was stirred at room temperature for 96 h and then poured into a mixture of 150 ml of water and 1 ml of glacial acetic acid. The mixture was stirred for 10 min and the organic layer was separated. The aqueous layer was extracted with 2×50 ml of ether. The organic layers were combined and washed successively with water and saturated NaCl solution and then dried ($M_gSO_4$). The solvent was removed in vacuo and the residue was purified by flash chromatography (silica; 10% ethyl acetate in hexane) to give the title compound as a pale yellow oil. PMR ($CDCl_3$): & 1.95 (3H, d, J-1.3 Hz), 2.21 (3H, d, J-1.2 Hz), 2.34 (3H, s), 5.90 (1H, broad S), 6.86- 6.93 (2H, m), 7.01 (1H, d, J-7.2 Hz), 7.24 (1H, t, J-7.2 Hz).

2-(1,1,3-Trimethyl-3-hydroxybutyl) 5-methyl-phenol (Compound 45)

To an ice-bath cooled suspension of 13 g (97.5 mmol) of aluminum chloride in 200 ml of methylene chloride was added dropwise under argon a solution of 9.0 g (47.4 mmol) of 3-methyl-phenyl-3,3-dimethylacrylate (Compound 44) in 100 ml of methylene chloride. The reaction mixture was stirred at 0 degrees C. for a further 30 min and then at room temperature for 15 h. The reaction mixture was poured into 200 ml of an ice water/salt mixture and the organic layer was separated. The aqueous layer was extracted with 50 ml of ether. The organic layers were combined and washed successively with water and saturated NaCl solution and then dried ($MgSO_4$). The solvent was removed in vacuo and the residue purified by flash chromatography (silica; 5% ethyl acetate in hexane) to give an approximately 2.5:1 mixture of isomeric products, 4,4,7-trimethyl-2-oxo-chroman and 4,4,5-trimethyl-2-oxo-chroman as a pale yellow oil. To a solution of 3.8 g (20 mmol) of this mixture of isomeric 2-oxo-chromans in 60 ml of ether at 0 degrees C. was added under argon 20 ml of 3.0M (60 mmol) of methyl magnesium bromide in ether. The reaction mixture was stirred at room temperature for 48 h and then poured onto a mixture of ice and 1 ml of conc. $H_2SO_4$. The organic layer was separated and the aqueous layer extracted with 2×50 ml of ether. The organic layers were combined and washed successively with water, saturated $NaHCO_3$ solution, water again and then saturated NcCl solution and then dried ($MgSO_4$). The solvent was removed in vacuo and the residue was purified by flash chromatography (silica; 15% ethyl acetate in hexanes) to give the title compound as a colorless oil. PMR ($CDCl_3$): & 1.14 (6H, s), 1.45 (6H, s), 2.19 (3H, s), 2.21 (2H, s), 6.39 (1H, d, J-1.8 HZ), 6.67 (1H, dd, J-7.9 Hz, 1.8 Hz), 7.16 (1H, d, J-7.9 Hz), 7.44 (1H, s).

2,2,4,4,7-Pentamethyl-chroman (Compound 46)

To 2.16 g (11.7 mmol) of 2-(1,1,3-trimethyl-3-hydroxybutyl) 5-methyl-phenol (Compound 45) was added under nitrogen 50 ml of 20% aqueous sulfuric acid. The reaction mixture was heated at reflux for 13 h and then cooled. The organic layer was separated and the aqueous layer was extracted with ether. The organic extracts were combined and washed successively with water, saturated $NaHCO_3$ solution, water again and saturated NaCl solution and then dried ($MgSO_4$). The solvent was removed in vacuo to give the title compound as a yellow oil. PMR ($CDCl_3$): & 1.32 (6H, s), 1.34 (6H, s), 1.81 (2H, s), 2.26 (3H, s), 6.63 (1H, s), 6.72 (1H, d, J-7.9 Hz), 7.15 (1H, d, J-7.9 Hz).

2,2,4,4,7-pentamethyl-6-acetyl-chroman (Compound 47)

To an ice-bath cooled solution of 1.96 g (9.6 mmol) of 2,2,4,4,7-pentamethyl-chroman (Compound 46) in 30 ml of nitromethane was added under argon 1.059 g (13.5 mmol) of acetyl chloride followed by 1.9 g (14.3 mmol) of aluminum chloride. The reaction mixture was stirred at room temperature for 14 h and then cooled in an ice-bath and treated with 25 ml of conc. HCl. The mixture was warmed to room temperature and diluted with ether and water. The organic layer was separated and the aqueous layer extracted with ether. The organic extracts were combined and washed successively with water, saturated $NaHCO_3$ solution, water again, and saturated NaCl solution, and then dried ($MgSO_4$). The solvent was removed in vacuo and the residue was purified by flash chromatography (silica; 5% ethyl acetate in hexanes) to give the title compound as a pale yellow oil. PHR ($CDCl_3$): & 1.36 (6H, s), 1.37 (6H, s), 1.86 (2H, s), 2.49 (3H, s), 2.56 (3H, s), 6.65 (1H, s), 7.74 (1H, s).

2,2,4,4,7-Pentamethyl-6-ethynyl-chroman (Compound 48)

To a solution of 455 mg (4.5 mmol) of disopropylamine in 5 ml of dry THF at −78 degrees C. was added under argon 3 ml of 1.5M n-BuLi in hexane. The mixture was stirred at −78 degrees C. for a further 45 min and then treated with a solution of 1.07 g (4.3 mmol) of 2,2,4,4,7-pentamethyl-6-acetyl-chroman (Compound 47) in 4 ml of dry THF. The reaction mixture was stirred at −78 degrees C. for 1 h and then treated with 776 mg (4.5 mmol) of diethyl chlorophosphate. The mixture was allowed to warm to room temperature and then transferred by a double-ended needle into a solution of lithium diisopropyl amide in 10 ml dry THF at −78 degrees C. which was prepared as described above using 910 mg (9.0 mmol) of diisopropylamine and 6 ml of 1.5M (9.0 mmol) n-BuLi in hexane. The mixture was stirred at room temperature fur 15 h and then poured into 10 ml of iced water. The mixture was acidified to pH=2 with 10% HCl solution. The organic layer was separated and the aqueous layer extracted with pentans. The organic extracts were combined and washed successively with water, saturated $NaHCO_3$ and saturated NaCl solutions and then dried ($MgSO_4$). The solvent was removed in vacuo and the residue purified by Kugelrohr distillation (82 degrees C., 0.3 mm) to give the title compound as a pale yellow oil. PMR ($CDCl_3$): & 1.32 (6H, s), 1.34 (6H, s), 1.81 (2H, s), 2.36 (3H, s), 3.18 (1H, s), 6.64 (1H, s), 7.40 1H (s). MS exact mass, m/e 228.1520 (calcd. for $C_{16}H_{20}O$, 228.1514).

Ethyl-6-[(2,2,4,4,7-pentamethyl-6-chromanyl)-ethynyl] nicotinate (Compound 7)

A solution of 300 mg (1.316 mmol) of 2,2,4,4,7-pentamethyl-6-ethynyl-chroman (Compound 48) and 245.6 mg (1.3276 mmol) of ethyl 6-chloro-nicotinate (Compound 29) in 2 ml of triethylamine was placed in a pressure tube and a stream of nitrogen was bubbled through the solution for 15 min. The tube was then flushed with argon and a finely ground mixture of 100 mg (0.1425 mmol) of his (triphenylphosphine) palladium (II) chloride and 50 mg (0.2625 mmol) of cuprous iodide was added to the solution. The pressure tube was then sealed and the reaction mixture heated at 60 degrees C. for 72 h. The mixture was cooled to room temperature and the triethylamine removed under vacuum. The residue was purified by flash chromatography (silica; 10% ethyl acetate in hexane) to give the title compound as a yellow solid. PMR (CDCl$_3$): & 1.37 (6H, s), 1.38 (6H, s), 1.44 (3H, t, J-7.2 Hz), 1.85 (2H, s), 2.49 (3H, s), 4.43 (2H, q, J-7.2 Hz), 6.70 (1H, s), 7.55-7.61 (2H, m), 8.28 (1H, dd, J-S.2 Hz, 2.1 Hz), 9.22 (1H, d, J-2.1 Hz). MS exact mass, m/e 377.1982 (calcd. for C$_{24}$H$_{27}$O$_3$N, 377.1991).

2-[2,2(4,4-tetramethylchroman-6-yl)ethynyl]-5-hydroxtmethylpyridine (Compound 50)

A 250 ml 3-necked flask is fitted with a stirrer, a dropping funnel, a nitrogen inlet and a thermometer. In the flask is placed a solution of 379.5 mg (10 mmol) of lithium aluminum hydride in 30 ml of dry diethyl ether. The solution is cooled to −65 degrees C. under nitrogen and a solution of 3.632 g (10 mmol) of ethyl 6-[(2,2,4,4-tetramethylchroman-6-yl)ethynyl]-nicotinate (Compound 43) in 15 ml of dry ether is added dropwise at a rate such that the temperature does not exceed −60 degrees C. The mixture is stirred at −30 degrees C. for 1 hour and the excess hydride is then destroyed by the addition of 300 mg (3.4 mmol) of ethyl acetate. The reaction mixture is then hydrolyzed by adding 3 ml of saturated ammonium chloride solution and allowing the temperature to rise to room temperature. The mixture is then filtered and the residue washed with ether. The ether layer is then washed with saturated solium chloride solution, dried (MgSO$_4$) and then concentrated in vacuo. The residue is purified by chromatograhy followed by recrystallization to give the title compound.

By the same process, acids or esters of this invention may be converted to their corresponding primary alcohols.

2-[2,2,4,4-tetramethylchroman-6-yl)ethynyl]-5-acetoxymethylpyridine (Compound 51)

A solution of 3.09 g (10 mmol) of 2,2,4,4-tetramethyl-6-[2-(5-hydroxymethylpyrid-2-yl)ethynyl]chroman (Compound 50) 600 mg (10 mmol) of glacial acetic acid, 2.06 g (10 mmol) of dicyclohexylcarbodiimide and 460 mg (3.765 mmol) of 4-dimethylaminopyridine in 150 ml methylene chloride is stirred at room temperature for 48 hours. The reaction mixture is then filtered and the residue washed with 50 ml of methlene chloride. The filtrate is then concentrated in vacuo and the residue is purified by chromatography followed by recrystallization to give the title compound.

Proceeding in the same manner, other alcohols of this invention may be esterified.

2-[(2,2,4,4-tetramethylchroman-6-yl)ethynyl]-pyridine-5-carboxaldehyde (Compound 52)

A solution of 1.396 g (11 mmol) of freshly distilled oxalyl chloride in 25 ml of methylene chloride is placed in a 4-necked flask equipped with a stirrer, a thermometer and two pressure-equalizing addition funnels fitted with drying tubes. The solution is cooled to −60 degrees C. and then treated dropwise with a solution of 1.875 g (24 mmol) of dimethyl sulfoxide (distilled from calcium hydride) in 5/ml of methylene chloride over a five minute period. The reaction mixture is then stirred at −60 degrees C. for an additional 10 minutes. A solution of 3.10 g (10 mmol) of 2,2,4,4-tetramethyl-6-[(5-hydroxymethylpyrid-2-yl)ethy- nyl]-chroman (Compound 50) in 10 ml of methylene chloride is then added to the reaction mixture over a period of 5 minutes. The mixture is stirred for a further 15 minutes and is then treated with 5.06 g (50 mmol) of triethylamine. The cooling bath is then removed and the mixture is allowed to warm to room temperature. Thirty ml of water is then added to the mixture and stirring is continued for a further 10 minutes. The organic layer is then separated and the aqueous layer is extracted with 20 ml of methylene chloride. The organic layers are then combined and washed successively with dilute HCl, water and dilute Na$_2$CO$_3$ solution and then dried (MgSO$_4$). The solution is then filtered and concentrated in vacuo and the residue is purified by chromatography followed by recrystallization to give the title compound.

Primary alcohols of this invention may be oxidized to their corresponding aldehydes by this method.

2-[(2,2,4,4-tetramethylchroman-6-yl)ethynyl]-5-(1-hydroxyropyl)pyridine (Compound 53)

Four ml of a 3M (12 mmol) solution of ethylmagnesium bromide in ether is placed in a 3-necked flask fitted with a mechanical stirrer, a reflux condenser protected by a drying tube and a pressure-equalizing dropping funnel protected by a drying tube. The flask is cooled in an ice bath and a solution of 2.98 g (10 mmol) of 2-[2,2,4,4-tetramethylchroman-6-yl) ethynyl]-pryidine-5-carboxaldehyde (Compound 52) in 10 ml of dry ether is added slowly with vigorous stirring. The cooling bath is then removed and the mixture heated at reflux for 3 hours. The mixture is then cooled in an ice-salt bath and 5 ml of saturated ammonium chloride solution added. The mixture is stirred for a further 1 hour and then filtered and the residue washed with two 10 ml portions of ether. The ether solution is then separated, dried (MgSO$_4$) and the ether removed in vacuo. The residue is then purified by chromatography followed by recrystallization to tive the title compound.

Using the same procedure any of the other aldehydes of this invention can be converted to the corresponding secondary alcohols.

Such secondary alcohols may be converted to their corresponding ketones using the procedure described for the preparation of Compound 52 or other oxidation procedures.

2-[(2,2,4,4-tetramethylchroman-6-yl)ethynyl]-5-dimethoxymethylpyridine (Compound 54)

A round-bottomed flask is fitted with a Dean-Stark apparatus under a reflux condenser protected by a drying tube. A mixture of 3.58 g (12 mmol) of 2-[2,2,4,4-tetramethylchroman-6-yl)-ethynyl]-pyridine-5-carboxaldehyde (Compound 52) 4.80 mg (15 mmol) of anhydrous methanol, 2 mg of p-toluenesulfonic acid monohydrate and 10 ml of anhydrous benzene is placed in the flask and the mixture heated at reflux under nitrogen until close to the theoretical amount of water is collected in the Dean-Stark trap. The reaction mixture is cooled to room temperature and extracted successively with 5 ml of 10% sodium hydroxide solution and two 5 ml portions of water and then dried (MgSO$_4$). The solution is then filtered and the solvent removed in vacuo. The residue is purified by chromatography and then recrystallization to give the title compound.

In a similar manner, any aldehyde or ketone of this invention may be converted to an acetal or a ketal.

Following the procedures set forth above, with such modificiation which will be readily apparent to a synthetic organic chemist of ordinary skill in light of the present disclosure, the following further examples of compounds can be prepared:

2,2,4,4-tetramethyl-6-acetyl-7-ethylchroman;
2,2,4,4-tetramethyl-6-acetyl-7-propylchroman;
2,2,4,4-tetramethyl-6-acetyl-7-butylchroman;
2,2,4,4-tetramethyl-6-acetyl-7-pentylchroman;
2,2,4,4-tetramethyl-6-acetyl-7-hexylchroman;
2,2-diethyl-4,4-dimethyl-6-acetyl-chroman;
2,2-diethyl,-4,4,7-trimethyl-6-acetyl-chroman;
ethyl 6-[(2,2,4,4-tetramethyl-7-ethylchroman-6-yl)ethynyl]nicotinate;
ethyl 6-[(2,2,4,4-tetramethyl-7-propylchroman-6-yl)ethynyl]nicotinate;
ethyl 6-[(2,2,4,4-tetramethyl-7-hexylchroman-6-yl)ethynyl]nicotinate;
ethyl [2-((2,2,4,4-tetramethylchroman-6-yl)ethynyl)-pyrid-5-yl]acetate;
ethyl [2-((2,2,4,4,7-pentamethylchroman-6-yl)ethynyl)-pyrid-5-yl]acetate;
ethyl [2-((2,2,4,4-tetramethyl-7-ethylchroman-6-yl)ethynyl)pyrid-5-yl]acetate;
ethyl [2-((2,2,4,4-tetramethyl-7-hexylchroman-6-yl)ethynyl)pyrid-5-yl]acetate;
ethyl 3-[2-((2,2,4,4-tetramethylchroman-2-yl)ethynyl)pyrid-5-yl]propionate;
ethyl 3-[2-((2,2,4,4,7-pentamethylchroman-6-yl)ethynyl)pyrid-5-yl]propionate;
ethyl 3-[2((2,2,4,4-tetramethyl-7-ethylchroman-6-yl)ethynyl)pyrid-5-yl]propionate;
ethyl 3-[2((2,2,4,4-tetramethyl-7-hexylchroman-6-yl)ethynyl)pyrid-5-yl]propionate;
ethyl 5-[2-((2,2,4,4-tetramethylchroman-6-yl)ethynyl)pyrid-5-yl]pentanoate;
ethyl 5-[2-((2,2,4,4,7-pentamethylchroman-6-yl)ethynyl)pyrid-5-yl]pentanoate;
ethyl 5-[2-((2,2,4,4-tetramethyl-7-ethylchroman-6-yl)ethynyl)pyrid-5-yl]pentanoate;
ethyl 5-[2-((2,2,4,4-tetramethylchroman-6-yl-ethynyl)pyrid-5-yl]pentanoate;
ethyl 5-[2-((2,2,4,4-tetramethylchroman-6-yl)ethynyl)-fur-2-yl]acetate;
ethyl [5-((2,2,3,3,7-pentamethylchroman-6-yl)ethynyl)fur-2-yl]acetate;
ethyl [5-((2,2,4,4-tetramethyl-7-ethylchroman-6-yl)ethynyl)-fur-2-yl]acetate;
ethyl [5-((2,2,4,4-tetramethyl-7-hexylchroman-6-yl)ethynyl-fur-2-yl]acetate;
ethyl 5-[5-((2,2,4,4-tetramethylchroman-6-yl)ethynyl)fur-2-yl]pentanoate;
ethyl 5-[5-((2,2,4,4,7-pentamethylchroman-6-yl)ethynyl)-fur-2-yl]pentanoate;
ethyl 5-[5-((2,2,4,4-tetramethyl-7-ethylchroman-6-yl)ethynyl)fur-2-yl]pentanoate;
ethyl 5-[5-((2,2,4,4-tetramethyl-7-hexylchoman-6-yl)ethynyl)fur-2-yl]pentanoate;
ethyl [5-((2,2,4,4-tetramethylchroman-6-yl)ethynyl)thien-2-yl]acetate;
ethyl [5-((2,2,4,4,7-pentamethylchroman-6-yl)ethynyl)thien-2-yl]acetate;
ethyl [5-((2,2,4,4-tetramethyl-7-ethylchroman-6-yl)ethynyl)thien-2-yl]acetate;
ethyl [5-((2,2,4,4-tetramethyl-7-hexylchroman-6-yl)ethynyl)thien-2-yl]acetate;
ethyl 5-[5((2,2,4,4-tetramethylchroman-6-yl)ethynyl)thien-2-yl]pentanoate;
ethyl 5-[5-((2,2,4,4,7-pentamethylchroman-6-yl)ethynyl)thien-2-yl]pentanoate;
ethyl 5-[5-((2,2,4,4-tetramethyl-7-ethylchroman-6-yl)ethynyl)thien-2-yl]pentanoate;
ethyl 5-[5-((2,2,4,4-tetramethyl-7-hexylchroman-6-yl)ethynyl)thien-2-yl]pentanoate;
ethyl [6-((2,2,4,4-tetramethylchroman-6-yl)ethynyl)-pyridazin-3-yl]acetate;
ethyl [6-((2,2,4,4,7-pentamethylchroman-6-yl)ethynyl)-pyridazin-3-yl]acetate;
ethyl [6-((2,2,4,4-tetramethyl-7-ethylchroman-6-yl)ethynyl)pyridazin-3-yl]acetate;
ethyl [6-((2,2,4,4-tetramethyl-7-hexylchroman-6-yl)ethynyl)pyridazin-3-yl]acetate;
ethyl 5-[6-((2,2,4,4-tetramethylchroman-6-yl)ethynyl)pyridazin-3-yl]pentanoate;
ethyl 5-[6-((2,2,4,4,7-pentamethylchroman-6-yl)-ethynyl)pyridazin-3-yl]pentanoate;
ethyl 5-[6-((2,2,4,4-tetramethyl-7-ethylchroman-6-yl)ethynyl)pyridazin-3-yl]pentanoate;
ethyl 5-[6-((2,2,4,4-tetramethyl-7-hexylchroman-6-yl)ethynyl)pyridazin-3-yl]pentanoate;
ethyl [5-((2,2,4,4-tetramethylchroman-6-yl)ethynyl)pyrimidin-2-yl]acetate;
ethyl [5-((2,2,4,4,7-pentamethylchroman-6-yl)ethynyl)pyrimidin-2-yl]acetate;
ethyl [5-((2,2,4,4-tetramethyl-7-ethylchroman-6-yl)ethynyl)pyrimidin-2-yl]acetate;
ethyl [5-((2,2,4,4-tetramethyl-7-hexylchroman-6-yl)ethynyl)pyrimidin-2-yl]acetate;
ethyl 5-[5-((2,2,4,4-tetramethylchroman-6-yl)ethynyl)pyrimidin-2-yl]pentanoate;
ethyl 5-[5-((2,2,4,4,7-pentamethylchroman-6-yl)ethynyl)pyrimidin-2-yl]pentanoate;
ethyl 5-[4-((2,2,4,4-tetramethyl-7-ethylchroman-6-yl)ethynyl)pyrimidin-2-yl]pentanoate;
ethyl 5-[5-((2,2,4,4-tetramethyl-7-hexylchroman-6-yl)ethynyl)pyrimidin-2-yl]pentanoate;
ethyl [5-((2,2,4,4-tetramethylchroman-6-yl)ethynyl)pyrazin-2-yl]acetate;
ethyl [5-((2,2,4,4,7-pentamethylchroman-6-yl)ethynyl)pyrazin-2-yl]acetate;
ethyl [5-((2,2,4,4-tetramethyl-7-ethylchroman-6-yl)ethynyl)pyrazin-2-yl]acetate;
ethyl [5-((2,2,4,4-tetramethyl-7-hexylchroman-6-yl)ethynyl)pyrazin-2-yl]acetate;
ethyl [5-[5-((2,2,4,4-tetramethylchroman-6-yl)ethynyl)pyrazin-2-yl]pentanoate;
ethyl 5-[5-((2,2,4,4,7-pentamethylchroman-6-yl)ethynyl)pyrazin-2-yl]pentanoate;
ethyl 5-[5-((2,2,4,4-tetramethyl-7-ethylchroman-6-yl)ethynyl)pyrazin-2-yl]pentanoate;
ethyl 5-[5-((2,2,4,4-tetramethyl-7-hexylchroman-6-yl)ethynyl)pyrazin-2-yl]pentanoate;
ethyl 6-[2,2-diethyl-4,4-dimethylchroman-6-yl)ethynyl]nicotinate; and
ethyl 6-[2,2-diethyl-4,4,7-trimethylchroman-6-yl)ethynyl]nicotinate.

Examples of Formulation for Topical Administration

Preferably the compounds of the invention may be administered topically using various formulations. Such formulations may be as follows:

| Ingredient | Weight/Percent |
| --- | --- |
| Solution | |
| Retinoid (active ingredient) | 0.1 |
| BHT | 0.1 |
| Alcohol USP | 58.0 |
| Polyesthylene Glycol 400 NF | 41.8 |
| Gel | |
| Retinoid (active ingredient) | 0.1 |
| BHT | 0.1 |
| Alcohol USP | 97.8 |
| Hydroxypropyl Cellulose | 2.0 |

What is claimed is:

1. Compounds of the formula

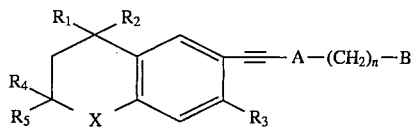

where X is NR', where R' is hydrogen or lower alkyl;

$R_1$, $R_2$ and $R_3$ are hydrogen or lower alkyl;

$R_4$ and $R_5$ are hydrogen or lower alkyl with the proviso that $R_4$ and $R_5$ both are not hydrogen;

n is an integer from 0 to 5;

A is thienyl or furyl, and

B is hydrogen, COOH or a pharmaceutically acceptable salt thereof, $COOR_8$, $COONR_9R_{10}$, —$CH_2OH$, $CH_2OR_{11}$, $CH_2OCOR_{11}$, CHO, $CH(OR_{12})_2$, $CHOR_{13}O$, —COR", $CR''(OR_{12})_2$, or $CR''OR_{13}O$, where R" is an alkyl group having 1 to 5 carbons, cycloalkyl having 3 to 5 carbons or alkenyl group having 2 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is lower alkyl, phenyl or lower alkylphenyl, $R_{12}$ is lower alkyl, $R_{13}$ is divalent alkyl radical of 2–5 carbons.

2. Compounds of claim 1 where A is thienyl, and n is 0, 1, or 2.

3. Compounds of claim 2 where n is O.

4. Compounds of claim 2 where B is COOH or a pharmaceutically acceptable salt thereof, $COOR_8$ or $COONR_9R_{10}$.

5. Compounds of claim 2 where $R_3$ is hydrogen or methyl.

6. Compounds of claim 2 where $R_4$ is the same alkyl group as $R_5$.

7. Compounds of claim 1 where A is furyl and n is 0, 1 or 2.

8. Compounds of claim 7 where n is 0.

9. Compounds of claim 7 where B is COOH or a pharmaceutically acceptable salt thereof, $COOR_8$ or $COONR_9R_{10}$.

10. Compounds of claim 7 where $R_3$ is hydrogen or methyl.

11. Compounds of claim 7 where $R_4$ is the same alkyl group as $R_5$.

12. A pharmaceutical composition comprising a therapeutically effective amount of one or more compounds set forth in claim 1 for the treatment of acne, Darier's disease, psoriasis, icthyoisis, eczema, atopic dermatitis, epithelial cancers, arthritic diseases, immunological disorders, dry eye syndrome, for promoting wound healing and reversing sun damage to the skin, the composition including a pharmaceutically acceptable excipient.

13. A pharmaceutical composition as set forth in claim 12, said composition being useful for treating skin disorders selected from the group consisting of acne, Darier's disease, psoriasis, icthyoisis, eczema, atopic dermatitis and sun damage to the skin, in a mammal.

14. A method for treating skin disorders selected from the group consisting of acne, Darier's disease, psoriasis, icthyoisis, eczema, atopic dermatitis and sun damage to the skin, in a mammal which method comprises administering alone or in conjunction with a pharmaceutically acceptable excipient, a therapeutically effective amount of one or more compounds set forth in claim 1.

15. The method of claim 14 used for treating psoriasis in a mammal.

16. Compounds of claim 1 where A is thienyl.

17. Compounds of claim 1 where A is furyl.

* * * * *

UNITED STATES PATENT AND TRADEMARK OFFICE
CERTIFICATE OF CORRECTION

PATENT NO. : 5,599,819
DATED : February 4, 1997
INVENTOR(S) : Chandraratna

Page 1 of 2

It is certified that error appears in the above-indentified patent and that said Letters Patent is hereby corrected as shown below:

Title page item [54] and col. 1, line 2-3, after "SUBSTITUED" please delete "CHROMANYL THIOCHROMANYL OR";

Title page 2, left column, after "5,234,926 8/1993 Chandraratna ...... 514/253" please add
--5,248,777 9/1993 Chandraratna .... 546/165--;

Column 1, line 3-4, after "SUBSTITUTED" please delete "CHROMANYL THIOCHROMANYL OR";

Column 7, line 20, "Scheme X" should be --Scheme I--;

Column 8, in Formula 21, please delete "Br";

Column 10, line 39, "[(CH$_2$)n-B" should be --[(CH$_2$)$_n$-B]--;

Column 15, line 9, "7.4.0" should be --7.40--;

Column 16, line 31, "J-S.1 Hz" should be --J-8.1 Hz--;

Column 17, line 39, "fur2" should be --fur-2--;

Column 19, line 16, "J-S.0 Hz" shoud be --J-8.0 Hz--;

Column 19, lines 55 and 56, two occurrences of "dH" should be --6H--;

Column 20, line 42, "J-S.4 Hz" should be --J-8.4 Hz--;

Column 21, line 57, "J-1.8 HZ" should be --J-1.8 Hz--;

Column 22, line 25, "PHR" should be --PMR--;

Column 22, line 48, "pentans" should be --pentane--;

Column 23, line 11, "J-S.2 Hz" should be --J-8.2 Hz--.

UNITED STATES PATENT AND TRADEMARK OFFICE
CERTIFICATE OF CORRECTION

PATENT NO. : 5,599,819
DATED : February 4, 1997
INVENTOR(S) : Chandraratna

It is certified that error appears in the above-indentified patent and that said Letters Patent is hereby corrected as shown below:

Column 13, line 56, "connectin" should be --connection--;

Column 16, line 59, "$C_{23} H_{25}$" should be --$C_{23}H_{25}$--;

Column 17, line 54, "5-[5-2,2,4,4-" should be ----5-[5-((2,2,4,4- --;

Column 17, line 64, "[6((2,2,4,4,7" should be --[6-((2,2,4,4,7- --;

Column 21, line 52, "NcCl" should be --NaCl--;

Column 22, line 45, "fur" should be --for--;

Column 22, line 55, "7.40 1H (s)" should be --7.40 (1H, s)--.

Signed and Sealed this

Third Day of March, 1998

*Attest:*

*Attesting Officer*

BRUCE LEHMAN

*Commissioner of Patents and Trademarks*